United States Patent
Janas et al.

(12) 
(10) Patent No.: US 6,667,049 B2
(45) Date of Patent: Dec. 23, 2003

(54) RELIC PROCESS FOR PRODUCING BIORESORBABLE CERAMIC TISSUE SCAFFOLDS

(75) Inventors: Victor F. Janas, Monroe Township, NJ (US); Kevor Shane TenHuisen, Clinton, NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/819,214

(22) Filed: Mar. 28, 2001

(65) Prior Publication Data

US 2001/0016353 A1 Aug. 23, 2001

Related U.S. Application Data

(62) Division of application No. 09/333,231, filed on Jun. 14, 1999.

(51) Int. Cl.⁷ .................. A61F 2/00; C12N 11/14; C12N 5/06; C12N 5/08; C12N 3/00
(52) U.S. Cl. .............. 424/423; 424/93.7; 435/176; 435/395; 435/399; 435/283.1; 435/284.1
(58) Field of Search ................ 435/176, 180, 435/395, 399, 283.1, 284.1; 424/423, 93.7

(56) References Cited

U.S. PATENT DOCUMENTS

| | | | | |
|---|---|---|---|---|
| 3,860,529 A | * | 1/1975 | Hamling | 252/301.1 R |
| 4,604,097 A | | 8/1986 | Graves et al. | 633/11 |
| 4,613,577 A | | 9/1986 | Tagai et al. | 501/35 |
| 4,655,777 A | | 4/1987 | Dunn et al. | 623/16 |
| 4,735,857 A | | 4/1988 | Tagai et al. | 428/388 |
| 4,820,573 A | | 4/1989 | Tagai et al. | 428/228 |
| 4,863,974 A | | 9/1989 | Mallouk et al. | 521/85 |
| 4,897,370 A | | 1/1990 | Horiguchi et al. | 501/5 |
| 5,013,323 A | | 5/1991 | Kobayashi et al. | 623/16 |
| 5,074,916 A | | 12/1991 | Hench et al. | 104/35 |
| 5,468,544 A | | 11/1995 | Marcolongo et al. | 428/224 |
| 5,486,359 A | | 1/1996 | Caplan et al. | 424/93.7 |
| 5,615,466 A | | 4/1997 | Safari et al. | 29/25.35 |
| 5,645,934 A | | 7/1997 | Marcolongo et al. | 428/357 |
| 5,721,049 A | | 2/1998 | Marcolongo et al. | 428/370 |
| 5,770,417 A | | 6/1998 | Vacanti et al. | 435/180 |
| 5,939,323 A | | 8/1999 | Valentini et al. | 435/395 |
| 6,004,500 A | * | 12/1999 | Safari et al. | 264/610 |
| 6,136,029 A | | 10/2000 | Johnson et al. | 623/16 |
| 6,283,997 B1 | * | 9/2001 | Garg et al. | 623/16.11 |
| 6,451,059 B1 | | 9/2002 | Janas et al. | 623/23.51 |

OTHER PUBLICATIONS

"Bone Graft and Bone Graft Substitutes: A Review of Current Technology and Applications": Damien and Parsons; J. Applied Biomaterials, vol. 2, 1991, pp 187–208.

Richard B. Cass, "Fabrication of Continuous Ceramic Fiber by the Viscous Suspension Spinning Process," Ceramic Bulletin, vol. 70, No. 3, 1991.

* cited by examiner

*Primary Examiner*—David M. Naff

(57) ABSTRACT

A relic process is used to produce bioresorbable ceramic scaffolds that can be used for in vitro or in vivo growth of human or animal tissue such as bone or cartilage. The process involves impregnating an organic fabric template with metal and phosphate ceramic precursors, heat treating the impregnated fabric to decompose the fabric to form a ceramic green body, and sintering the ceramic green body to form the scaffold which has a form analogous to that of the fabric template. Impregnating the fabric may be by soaking the fabric in a solution or sol containing the ceramic precursors. The fabric may be formed into a laminate prior to heat treating. Sintering results in fibers of the fabric being cross-sintered with one another to form a three-dimensional scaffold structure having controlled pore size and distribution. The scaffold may be treated with a material that promotes bone growth through the scaffold.

8 Claims, 2 Drawing Sheets

1 mm

100 μm

RELIC PROCESS FOR PRODUCING BIORESORBABLE CERAMIC TISSUE SCAFFOLDS

This application is a divisional of pending U.S. Ser. No. 09/333,231, filed Jun. 14, 1999.

FIELD OF THE INVENTION

The present invention relates to resorbable ceramic scaffolds for use in biological applications, and their method of production. Specifically, this invention relates to novel scaffolds, formed via a replication, or relic technique, and useful as biological replacements for hard tissue.

BACKGROUND OF THE INVENTION

Bone grafts formed of porous calcium phosphates (CaP) show potential as a scaffolding for the growth of new bone in applications such as spinal fusion, long bone fractures, non-union fractures, bone defects, and hip revisions. In current medical devices, the porosity is either randomly distributed, or the manufacturing techniques have limited ability to control pore size. Control of pore distribution and size may be advantageous in optimizing bone growth into the graft.

Bone grafts are used in the repair of significant fractures, the treatment of skeletal tumors, spinal fusion, and the reconstruction of failed total arthroplasties. Autogenous bone, or autograft, is bone harvested from another location in the patient, and used as the graft. Autograft performs very well in the applications cited above. The disadvantages of autograft include the limited supply of excess bone in the patient, as well as the inherent risks of morbidity and recovery pain taken by performing a second surgery. Allograft, bone taken from another human, has the advantage of being in larger supply than autograft bone. However, the greater immunogenic response of allograft, and risk of viral contamination or risk of transmission of live virus to the recipient, have led to the decline in use of allograft bone as a bone graft material. Xenograft, or bone grafts taken from another species, often elicits acute antigenic response. In the vast majority of cases, xenograft fails in its role as a graft material.

Synthetic bone graft materials have been described in *Bone Graft and Bone Graft Substitutes: A Review of Current Technology and Applications;* Damien and Parsons; *J. Applied Biomaterials,* Vol. 2, 1991, pages 187–208, which is incorporated herein by reference. The ideal graft should be able to support a load equivalent to the bone that is being replaced, so that the newly formed bone can remodel to the same quality and dimensions of the original bone that is being replaced. Ideal graft is also osteoactive, enhancing the formation of new bone. This is achieved both by the chemical nature of the material, as well as the structure, or architecture of the graft. Structurally, the graft needs to be porous to allow for ingrowth of the new bone. Though no optimal pore size has been established, the size of the pores required for good bone growth is between 100 and 500 microns. The ability to tailor the pore size and distribution is also viewed as a method of enhancing bone growth. Load support can be achieved by having the supporting phase of the graft three-dimensionally connected.

The materials in bone graft substitutes include, but are not limited to, plaster of Paris (calcium sulfate, $CaSO_4 \cdot 1/2H_2O$), tricalcium phosphate ($Ca_3(PO_4)_2$), hydroxyapatite ($Ca_{10}(PO_4)_6(OH)_2$), calcium phosphate cements, calcium aluminates, the family of Bioglass® (composed of $SiO_2$, $Na_2O$, $CaO$, and $P_2O_5$), apatite-wollastinite glass-ceramics (AWGC), polymers such as polymethylmethacrylate (PMMA) or polyhydroxyethylmethacrylate (PHEMA), and blends of the above. They may be in the form of loose particles, particles bound in polymer or other carrier material (a paste), ceramic precursors that react when blended together (calcium phosphate cements), porous solids, or loose fiber constructs (such as felts), or textile processed fibers (weaves, braids, or knits).

The disadvantages of using loose particles as a bone graft include the difficulty of handling them, the tendency of the particles to settle (or pack tightly) into the defect, the inability of loose particles to support load, and particle migration away from the defect site in bodily fluids. Particle settling results in two problems. First, when the particles pack together, the pore size is reduced in the graft to less than 100 $\mu$m. This pore size does not allow the migration and ingrowth of cells into the graft. Particle settling also results in an inability to control the pore size and distribution in these systems. The size and distribution of pores in these types of grafts are determined by the size of the particles and how they pack together. Since settling is not controllable, there is no ability to use graft architecture to control new bone growth into the graft.

Particle migration from the sight results in possible tissue irritation and undesired tissue response in the regions were the particles eventually settle.

Particle settling and migration problems have been mitigated to some extent by the use of synthetic or natural matrix materials, including polymers such as PMMA, polysulfone (PS), or polyethylene (PE), which are not resorbable, and ceramics, such as plaster of Paris. Particles have also been enclosed in tubes of resorbable polymers, such as collagen or polyglycolide. The size and distribution of pores in these types of grafts are also not controllable. The distribution is determined by the size of the particles, how they pack together, and the space between them caused by the carrier matrix. As with loose particles, there is limited ability to use graft architecture to control new bone growth into the graft. Load support is also limited, since the graft substitute is in the form of a soft paste, and the load-supporting phase of the graft is not three-dimensionally connected.

For bone grafts in the form of cements, there is also a limited ability to control the pore size and distribution. Pore creating agents may be put into the cement prior to its formation. However, the size and distribution of pores are determined by the size, form, and concentration of the agent, resulting in the inability to use graft architecture to control new bone growth into the graft. This inability to control pore size and distribution also results in limits in load support capability. A random distribution of pores results in a random distribution of defects in the structure. So, although the load-supporting phase of the graft is three-dimensionally connected, these types of grafts have shown low load support capability.

Control of the pore size and distribution in porous solid bone grafts is also limited. Porous solid bone grafts have been formed using the replamine process on naturally occurring coral. Here, the pore size and distribution is limited to that of the species of coral used. Defect location is also uncontrollable, lowering the load support capability of the graft in a fashion similar to that discuss above for cements. Pore creating agents may also be put into a ceramic prior to its formation. But, as is the case with cements, the size and distribution of pores are determined by the size, form, and concentration of the agent.

Bone grafts in the form of textile architectures, such as weaves, braids, or knits, have advantages over the other forms of bone grafts. Textile technology may by used to precisely place the fibers in a desired location in space, allowing for a large degree of control in the size and distribution of pores in the bone graft structure. However, since there is no interconnection of fiber in three dimensions, load support capabilities of grafts of this type are limited.

There are a number of woven structured formed with fibers composed of the materials found in bone graft substitutes cited in the prior art. Tagai et al., in U.S. Pat. Nos. 4,820,573, 4,735,857, and 4,613,577, disclose a glass fiber provided for the filling of a defect or hollow portion of a bone. In this case, the calcium phosphate glass fiber may be in the form of short fibers, continuous fiber, or woven continuous fibers. In this prior work, the load support capability of the graft is limited since there is no interconnection of fiber in three dimensions.

To increase the strength of the fibrous implants, bioresorbable fibrous constructs have been filled with polymers to form composite structures. Many of these have been cited in the prior art. U.S. Pat. No. 5,013,323, to Kobayashi et al., discloses an implant material for replacing hard tissue composed of calcium phosphate glass fibers in an organic polymer, where some of the glass fiber on the composite surface is exposed to the living tissue to promote bonding of the device to the tissue.

In U.S. Pat. Nos. 5,721,049, 5,645,934, and 5,468,544 (all to Marcolongo et al.), disclose composite materials formed from bioactive glass or ceramic fibers. The preferred embodiments are braids or meshes of bioactive glass or ceramic fiber interwoven with structural, non-bioactive fibers impregnated with a polymer to form a composite of suitable biocompatibility and structural integrity. The braid or mesh is designed so that the bioactive fibers are concentrated on the surface of the implant.

A method of producing biodegradable prostheses comprising a composite of resorbable fibers reinforcing a biodegradable matrix is disclosed in U.S. Pat. Nos. 4,655,777 (Dunn & Kasper), and 4,604,097 (Graves & Kumar). The fibers include ceramic powders, β-tricalcium phosphate, and a biodegradable glass. In this case, the fiber/polymer composite is made in the laminated form, and not as a woven structure.

The limitation of the composite approach is that by filling in the space between the fiber, the structures themselves are no longer porous. So, they are unable to support the ingrowth of new bone. As discussed earlier, pore creating agents may also be put into the composite prior to its formation. However, as pointed out for earlier structures, the size and distribution of pores are determined by the size, form, and concentration of the agent.

The fibers produced in the patents cited above have a wide variety of compositions, and were formed by various techniques. In most cases, they are composed of mixtures of silicon dioxide ($SiO_2$), aluminum oxide ($Al_2O_3$), calcium oxide (CaO), sodium oxide ($Na_2O$), potassium oxide ($K_2O$), lithium oxide ($Li_2O$), magnesium oxide (MgO), zinc oxide (ZnO), strontium oxide (SrO), iron oxide ($Fe_2O_3$), titanium oxide ($TiO_2$), zirconium oxide ($ZrO_2$), calcium fluoride ($CaF_2$), and phosphorous pentoxide ($P_2O_5$). These compositions are melt spun at temperatures between 800 and 1700° C. A discussion of the range of spinnable, degradable glass compositions, and how they are processed, is discussed in U.S. Pat. No. 4,604,097 (Graves & Kumar).

The forming of bioactive ceramic bodies from precursor solutions has also been previously discussed. In one work (U.S. Pat. No. 5,074,916 to Hench et al.), alkali-free bioactive compositions were prepared by a sol-gel route. In this approach, alkoxysilane and calcium nitrate are dissolved in a blend of water and nitric acid. After a period of time, the solution forms a gel, which is dried and heat treated to yield a fine calcium-silicate-phosphate glass powder. The powder can be remelted and formed into final shape using traditional glass processing techniques. The inventors claim process, compositions, and powders forms of the glass. No mention is made, however, of the ability to control the pore size and distribution in the final device.

In another patent (U.S. Pat. No. 4,897,370, to Horiguchi et al.), a process for preparing bioceramic composite sintered bodies is claimed. Here, the starting materials are silicic acid ester, alkyl phosphates, calcium alkoxyls, and inorganic particulates and/or whiskers. The inorganic phase is used as reinforcement to the glass or glass-ceramic phase formed by reaction of the precursors. The above mention materials are mixed in water in a sequence which results in gelation of the mixture. The gel is dried, compacted, and sintered to yield the composite body. As in other prior art, no mention is made of the ability to control the pore size and distribution in the final device.

In summary, the prior art presents a number of methods for forming synthetic bone grafts. In all cases, the forming techniques lack the ability to tailor the pore size and distribution in the graft, and/or the ability to have the supporting phase of the graft three-dimensionally connected. Tailored pore size is viewed as a method of enhancing bone growth, while improved load support is achieved by a three-dimensionally connected supporting phase.

It is therefor an object of the present invention to provide a bone graft in which the pore size and distribution is tailored to enhance bone growth, and improved load support is achieved by a three-dimensionally connected support phase.

Another object of this invention is to create structures to use as scaffolds for the in vitro or in vivo growth of human or animal tissue, such as bone or cartilage. These scaffolds can be used as implant materials for the replacement of defects or hollow portions of hard tissue resulting from external injury or surgical removal of hard tissue tumors. Their composition can be tailored such as to be resorbed by the body at a rate equivalent to the rate at which natural hard tissue grows into the above mentioned defects or hollow portions of hard tissue.

A still further object of this invention is the formation of laminated bioresorbable structures where each layer has controlled pore size and distribution. This type of structure has another degree of control for optimizing bone growth into the resorbable ceramic structure if the structure is used as bone graft.

SUMMARY OF THE INVENTION

We have discovered a process for making three-dimensionally connected bioresorbable ceramic structures for use as bone replacement materials in which pore size and distribution are controlled. The process comprises impregnating an organic fabric with a metal and phosphate ceramic precursors that will provide a bioresorbable ceramic when sintered; heat treating the structure to decompose the organic fabric and any nitrates that may be present to form an unsintered biocompatible ceramic implant device. The unsintered device may thereafter be sintered to form a bioresorbable ceramic. The advantage of this work over biocompatible inorganic structures disclosed in the past is the ability to both control pore size and distribution for optimized bone ingrowth, as well as for a three-dimensionally connected ceramic structure with load support capability.

DETAILED DESCRIPTION OF THE INVENTION

Figure 1:
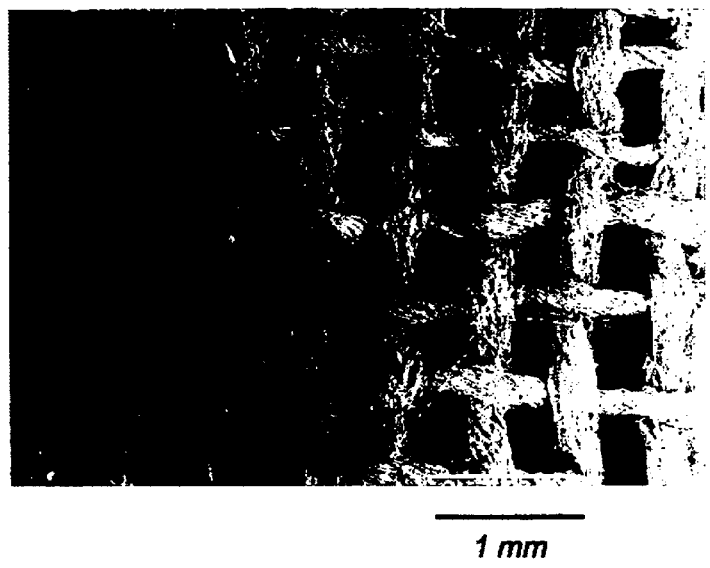
FIG. 1 is a photomicrograph at low magnification of a woven bioceramic structure.

In the present invention, a process for forming hard tissue scaffold is disclosed. The scaffold is formed by impregnating an organic template with a metal and phosphate ceramic precursor. The template is preferably a porous organic material that may be soaked in a solution or sol. When the pores of the porous organic material have been filled with the solution or sol the template is dried to remove the solvent, leaving behind the precursors in the proper composition. The dried template is then exposed to a heat to remove the organic material resulting in a green ceramic structure in the form of the template. The heat treatment is generally conducted in air or an oxygen rich environment to oxidize the organic material to $CO_2$ or $CO$. The green ceramic template is then heat treated in a second heat treating step to form the final structure. During the second heat treating step the precursors that were originally impregnated into the surface of the organic material or in the pores of the template, react to form the final body. The body will have an architecture that is analogous to the architecture of the original template. This process is generally referred to in industrial ceramics as the relic process. However, this process has never been applied to making absorbable medical devices.

Using the relic process with sol-gel techniques similar to those discussed in the background allows for the creation of bioresorbable ceramic structures in which the size and distribution of interconnected pores are controlled. For example, this process allows for the creation of woven calcium phosphate (CaP) structures, where the individual CaP filaments are on the order of 5–200 $\mu$m.

The inventive process starts with a template material that oxides at a temperature less than the sintering temperature of the ceramic precursors leaving substantially no residue. Generally, the templates materials are porous organic materials. Examples of suitable organic template materials include but are not limited to rayon, cotton, polyester (i.e. PET, PBT, polylactide, polyglycolide, polycaprolactone, etc.) and combination thereof. Preferred are organic materials with high surface areas. Currently preferred are commercially available activated novoloid-derived carbon fiber templates, including, but not limited to, the ACC-series available from American Kynol, Pleasantville, N.Y.

The organic materials are then impregnated with the ceramic precursors that will provide the desired bioresorbable ceramic. The organic materials are generally impregnated by soaking the templates in a CaP precursor solution either before or after arrangement into the desired structure. They are dried at low temperature to remove any solvents. After drying, the template structure is heated in air to a high enough temperature to oxidize the activated carbon to carbon monoxide and dioxide, leaving the CaP precursors to react and form a ceramic while maintaining the shape of the structure. The ceramics are sintered to the final density by increasing the temperature of the structure.

There are a number of phosphorus sources that can be used in this process. Depending on the exact combination of calcium, phosphorous and solvent, they either form an extremely fine colloidal precipitate or they form a meta-stable solution with the calcium source. These phosphorous sources include, but are not limited to, triethyl phosphate, triethylphosphite, alkoxides of phosphorus including both phosphate $[(R_1O)_3PO]$ and phosphites $[(R_2O)_3P]$ where R is an organic functional group, phenyl dichlorophosphine, phenyl dichlorophosphate, or any organophosphate that can be dissolved into or are miscible in a solvent, $H_3PO_4$ (and its hydrates including polyphosphoric acid), $H_3PO_3$, $P_2O_5$, $H_4P_2O_7$, all varieties of condensed phosphates that can be dissolved into a solvent and combination thereof.

Calcium sources include, but are not limited to calcium nitrate (and it's hydrates), calcium acetate (and it's hydrates), calcium nitrite (and it's hydrates); sugar complexes of calcium such as calcium gluconate and calcium saccharate; organic salts of calcium (and their hydrates) such as calcium 2-ethylbutanoate, calcium levulinate, calcium formate, calcium ascorbate, calcium citrate, calcium lactate, and calcium tartrate; calcium alkoxides $[Ca(OR_3)_2]$ were $R_3$ is an alkyl group such as in calcium methoxide, calcium ethoxide and combinations thereof.

Solvent choices typically are polar solvents that, upon evaporation/boiling, will not leave residuals. These include, but are not limited to alcohols, ketones, esters, and water.

The choice of solvent/calcium source/phosphorus source will be determined by the source's solubility in solvent and the metastability of the system once the phosphorus and calcium solutions have been combined.

The advantage of this work over the woven biocompatible inorganic structures disclosed in the past is that these structures are woven in the precursor state prior to CaP formation and sintering. When fired, the fibers will cross-sinter with one another, resulting in a three-dimensionally connected tissue scaffold structure in which pore size and distribution are controlled.

The structures created by this invention may be used as scaffolds for the in vitro or in vivo growth of human or animal tissue, such as bone or cartilage. These scaffolds can be used as implant materials for the replacement of defects or hollow portions of hard tissue resulting from external injury or surgical removal of hard tissue tumors. Their composition can be tailored by varying the composition of the scaffold such as to be resorbed by the body at a rate equivalent to the rate at which natural hard tissue grows into the above mentioned defects or hollow portions of hard tissue.

With this invention, there is opportunity for the formation of laminated structures, and a countless number of three-dimensional structures. The individual plies can be formed via textile operations such as weaving, braiding and knitting. Mixed fabric types can be incorporated into the structure for further control of pore size and distribution. Though no optimal pore size and distribution has been established, the size of the pores required for good bone growth is between 100 and 500 microns. The ability to tailor the pore size and distribution is also viewed as a method of enhancing bone growth.

In addition, the three-dimensional structure may be filled with resorbable synthetic polymers or biopolymers or ceramic materials that may or may not contain materials that promote bone growth through the device. These include autograft, allograft, or xenograft bone, bone marrow, demineralized bone (DBM), natural or synthetic bone morphogenic proteins (BMP's i.e. BMP 1 through 7), bone morphogenic-like proteins (i.e. growth and differentiation factor 5 (GFD-5) also known as cartilage-derived morphogenic factor 1, GFD-7 and GFD-8) epidermal growth factor (EGF), fibroblast growth factor (FGF i.e. FGF 1 through 9), platelet derived growth factor (PDGF), insulin like growth factor (i.e. IGF-I and IGF-II and optionally IGF binding proteins), transforming growth factors (TGF-β i.e. TGF-β I through III), vascular endothelial growth factor (VEGF) or other osteoinductive or osteoconductive materials known in the art. Biopolymers could also be used as conductive or chemotactic materials, or as delivery vehicles for growth factors. Examples could be recombinant or animal derived collagen gelatin or elastin. Bioactive coatings or surface treatments could also be attached to the surface of the device. For example, bioactive peptide sequences (RGD's) could be attached to facilitate protein adsorption and subsequent cell tissue attachment. Antibiotics could also be coated on the surface of the device or delivered by a material within the device.

The polymeric materials filling the device could exist in a number of phases including solids, foams, or liquids. The structure could be filled with polymer to some specified degree to improve the mechanical toughness of the device. Foamed polymeric materials could be lyophilized within the structure providing a scaffold within a scaffold. The porous polymeric foam would provide an osteoconductive medium for bone growth into the device. The porous foam could also serve as a delivery medium for growth factors, peptides, and other bioactive materials. The structure could also be filled with liquid polymers containing biological agents, with the entire structure acting to control the release rate of the agent.

The three-dimensional structure could also be filled with photocurable polymeric materials and cured in place with UV light source. It could also be filled with ceramic cements, monolithic ceramic materials or particles that are osteoconductive or inductive. The structure could also be post-processed with a ceramic or polymeric coating that is osteoconductive or inductive. The second ceramic material would act as a coating that would be different from the materials used for the main body of the scaffold.

The three-dimensional structure may also serve as a scaffold for the engineering of bone tissue to facilitate bone healing. The structure may have an internal porous structure that would be conducive to the growth of cells. As outlined in previous patents (Vacanti, U.S. Pat. No. 5,770,417), tissue can be harvested from a patient and the tissue can be sterile processed to provide a specific cell type (i.e., osteoblast, mesenchymal stem cell (Caplan, U.S. Pat. No. 5,486,359), etc.). The cells could contain inserted DNA encoding a protein that could stimulate the attachment, proliferation or differentiation of bone tissue. The three-dimensional structure would be placed in cell culture and the cells seeded onto or into the structure. The structure would be maintained in a sterile environment and then implanted into the donor patient once the cells have invaded the microstructure of the scaffold. The in vitro seeding of cells could provide for a more rapid healing process. Additionally, radio-opaque markers may be added to the scaffold to allow imaging after implantation.

Without intending to limit it in any manner, the present invention will be more fully described by the following examples.

EXAMPLE 1

Calcium nitrate tetrahydrate ($CaNO_3.4H_2O$) was dissolved in a solution consisting of triethyl phosphate $\{(C_2H_5O)_3P(O)\}$ and ethanol ($C_2H_5OH$) by stirring. The viscosity of this solution was controlled by changing the proportion of ethanol. Squares of activated carbon fabric (Code ACC-507-15) from American Kynol, Inc., Pleasantville, N.Y.) were soaked in the solution for several minutes. The fabric is a plain weave with a specific surface area of approximately 1,500 $m^2$/gm. After soaking, the squares were dried at 150° C. to remove the ethanol and initiate the reaction between the calcium nitrate tetrahydrate and triethyl phosphate. A weight gain of approximately 175% was measured for the dried fabric. The Soak-Dry cycle was repeated, and a weight gain of approximately 250% was measured for the fabric treated twice. Samples of fabric soaked once or twice were heat treated in a tube furnace (in an air atmosphere) as follows: Room temperature to 600° C. in two hours, hold 600° C. for twenty two hours, 600° C. to 1200° C. in two and one-half hour, hold 1200° C. for two hours, cool to 200° C. in two hours, remove from furnace. Firing shrinkage is approximately 50%.

FIG. 1 is an SEM photograph of the fired calcium phosphate relic resulting from a twice soaked template. The figure shows the large pores (100–500 μm) which have been associated with good tissue growth into a scaffold.

Figure 2:
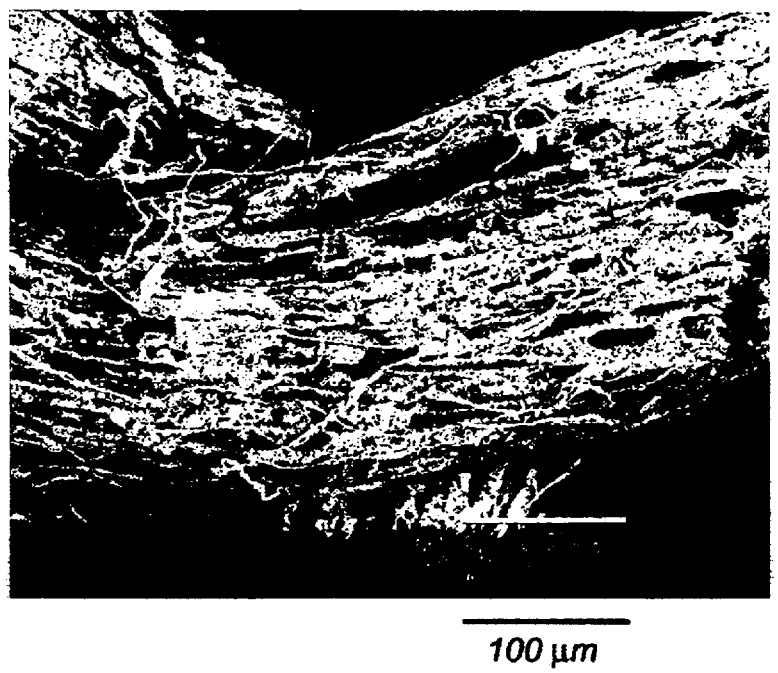
FIG. 2 is a photomicrograph of a section of FIG. 1 but taken at a higher magnification.

FIG. 2 shows the same scaffold at a higher magnification. In this SEM, individual ceramic fibers (10–20 μm diameter) are clearly visible, as are the fine pores (<10 μm) in and between the fibers. A higher firing temperature is expected to increase the density of these fibers.

We claim:

1. A process for making biocompatible, bioresorbable ceramic implant device comprising a resorbable hard tissue scaffold, comprising:

a) impregnating an organic fabric with at least one metal ceramic precursor and at least one phosphate ceramic precursor, b) heat treating the organic fabric to oxidize the fabric and form a biocompatible, bioresorbable ceramic green body, and c) sintering the biocompatible, bioresorbable ceramic green body, thereby forming said resorbable hard tissue scaffold.

2. The process of claim 1 wherein the organic fabric is impregnated by soaking the organic fabric in a solution or sol containing the at least one metal ceramic precursor and at least one phosphate ceramic precursor.

3. The process of claim 1 wherein prior to heat treating, the organic fabric is formed into a laminate.

4. The process of claim 1 wherein the fabric is formed by a textile operation selected from the group consisting of weaving, braiding, knitting and combinations thereof.

5. The process of claim 1 wherein the phosphate ceramic precursor is selected from the group consisting of triethyl phosphate, triethylphosphite, alkoxides of phosphorus, phenyl dichlorophosphine, phenyl dichlorophosphate, $H_3PO_4$, $H_3PO_4$ hydrates, $H_3PO_3$, $P_2O_5$, $H_4P_2O_7$, and combinations thereof.

6. The process of claim 1 wherein the metal ceramic precursor is selected from the group consisting of calcium nitrates, calcium acetates, calcium nitrites, sugar complexes of calcium, organic salts of calcium, calcium alkoxides and combinations thereof.

7. The process of claim 6 wherein the calcium alkoxide is $Ca(OR_3)_2$ wherein $R_3$ is an alkyl group.

8. The process of claim 1 wherein after the resorbable hard tissue scaffold is formed, the resorbable hard tissue scaffold is treated with a material that promotes bone growth through the scaffold.

* * * * *